United States Patent
De Medina et al.

(10) Patent No.: US 10,092,577 B2
(45) Date of Patent: Oct. 9, 2018

(54) STEROL DERIVATIVES FOR TREATING NEUROSENSORY HEARING LOSS, AND CORRESPONDING COMPOSITION

(71) Applicant: AFFICHEM, Toulouse (FR)

(72) Inventors: Philippe De Medina, Colomiers (FR); Michaël Paillasse, Toulouse (FR); Mats Ulfendahl, Stockholm (SE)

(73) Assignee: Affichem, Toulouse (FR)

( * ) Notice: Subject to any disclaimer, the term of this patent is extended or adjusted under 35 U.S.C. 154(b) by 0 days.

(21) Appl. No.: 15/329,190

(22) PCT Filed: Jul. 28, 2015

(86) PCT No.: PCT/FR2015/000164
§ 371 (c)(1),
(2) Date: Feb. 24, 2017

(87) PCT Pub. No.: WO2016/016518
PCT Pub. Date: Feb. 4, 2016

(65) Prior Publication Data
US 2017/0209465 A1    Jul. 27, 2017

(30) Foreign Application Priority Data

Jul. 30, 2014  (FR) .................................... 14 01755

(51) Int. Cl.
*A61K 31/58* (2006.01)
*A61K 31/575* (2006.01)

(52) U.S. Cl.
CPC ............ *A61K 31/58* (2013.01); *A61K 31/575* (2013.01)

(58) Field of Classification Search
CPC .............................. A61K 31/58; A61K 31/575
See application file for complete search history.

(56) References Cited

U.S. PATENT DOCUMENTS 7,947,668 B2 * 5/2011 Poirot ..................... C07J 43/00
514/176

* cited by examiner

*Primary Examiner* — Zohreh A Fay
(74) *Attorney, Agent, or Firm* — Studebaker & Brackett PC

(57) ABSTRACT

The invention relates to a composition for preventing bearing loss in subject or for at least partially restoring bearing in a subject having a reduced auditory function. The composition comprises at least one sterol compound inducing neuron differentiation. Said composition is placed in contact with at least part of the cochlea.

15 Claims, 3 Drawing Sheets

| R1 | R2 | R6 | Z1 | R4 | Protection: 100%-(treated threshold J42 - treated threshold J0)/(control threshold J42 - treated threshold J0) | | SGN Density (/10000μm²) |
|---|---|---|---|---|---|---|---|
| | | | | | Ex 1 | Ex 2 | Ex 2 |
| H | OH | -(CH₂)₃NH(CH₂)₄NH₂ | 1 | H | 101 ± 7 | 78 ± 12 | 2.6 ± 0.3 |
| H | OH | -(CH₂)₂-imidazol-4-yl | 0 | H | 96 ± 5 | 16 ± 4 | 2.6 ± 0.2 |
| Ac | OH | -(CH₂)₂-imidazol-4-yl | 0 | H | 96 ± 6 | 18 ± 7 | 2.7 ± 0.4 |
| H | OH | -(CH₂)₃NH(CH₂)₄NH₂ | 0 | 22-OH | 101 ± 4 | 75 ± 13 | 2.5 ± 0.6 |
| H | OH | -(CH₂)₃NH(CH₂)₄NH₂ | 0 | 27-OH | 100 ± 8 | 74 ± 10 | 2.4 ± 0.7 |
| H | OH | -(CH₂)₃NH(CH₂)₄NH(CH₂)₃NH₂ | 0 | H | 101 ± 6 | 74 ± 7 | 2.8 ± 0.4 |
| H | OH | -(CH₂)₃NH(CH₂)₄NH₂ | 0 | H | 102 ± 9 | 78 ± 8 | 2.7 ± 0.5 |

Table 1

STEROL DERIVATIVES FOR TREATING NEUROSENSORY HEARING LOSS, AND CORRESPONDING COMPOSITION

The present invention relates to the management of hearing loss. More precisely, the present invention relates to the use of a molecule of formula I or a pharmaceutically acceptable salt of such a compound; the composition according to the invention is administered to a subject in order to prevent hearing loss or to restore hearing in said subject.

Hearing loss is a common condition affecting more than 360 million people globally (World Health Organisation-2012). The hearing loss taken into consideration by the World Health Organisation is a loss greater than 25 dB. This pathology has significant adverse consequences (both economical and emotional) for the individuals affected and for society (de Graaf et al., Psychosom Med 64, 61-70), (Fellinger et al., Acta Psychiatr Scand 115, 243-5), (Fellinger et al., Soc Psychiatry Psychiatr Epidemiol 40, 737-42), (Mohr et al., Policy Anal Brief H Ser 2, 1-4). Numerous factors, such as age (50% of humans more than 65 years old, and 80% of those more than 75 years old are affected), noise, physical or emotional traumas, or else genetic factors, can be at the root of the dysfunction or loss of the hair cells followed by the degeneration of the auditory nerve, leading to hearing loss.

It is known that, in a non-injured auditory organ, sound is transmitted to special cells of the brain by the vibration of the eardrum, which transmits the information mechanically to the inner ear. In the inner ear, there are hair cells (referred to as HCs hereinafter), which transform said mechanical signals into electrical signals, which generate electrical information transmitted to the brain by spiral ganglion neurons (referred to as SGNs hereinafter). The hair cells are carried by a spiral-shaped organ referred to as the cochlea; the cochlea comprises two spiral chambers disposed side-by-side and filled with liquids (perilymph in one and endolymph in the other); the hair cells are disposed between these two chambers.

Medium or severe neurosensory hearing loss can be caused by at least three types of dysfunctions. Firstly the dysfunction or partial loss of the sensory HCs, secondly the degeneration of the axons of the spiral ganglion neurons (referred to hereinafter as SGNs for short), which transmit the signal of the HCs to the brain (auditory neuropathy), and thirdly the destructuring of the synaptic connections between the HCs and the SGNs (auditory synaptopathy). These different mechanisms leading to hearing loss are illustrated in FIG. 1, which will be discussed in detail further below in the present description.

In the case of loss of the hair cells, the signal can be transduced by a cochlear implant, the electrodes of which replace the HCs; in humans, in such a case the SGNs degenerate, more especially losing their axons pointing towards the HCs, but they do not die. The key to maintaining or restoring hearing thus lies in axon regrowth, which makes it possible to re-establish the connections between the SGNs and the transducers receiving the sound signal, whether HCs or a cochlear implant.

For deafness linked to the loss of HCs, cochlear implants alone improve hearing, but their efficacy is directly impacted by the integrity of the SGNs, the degeneration of which is not prevented by said implants; axon regrowth enabling a reduction of the distance between the nerve endings and the electrodes thus constitutes an interesting approach for improving the efficacy of cochlear implants (Shibata et al., Hear Res 281, 56-64). For any other form, there is not currently any satisfactory palliative or curative solution. The neurotrophic factors, which are the only molecules to have demonstrated a beneficial effect on neuron survival and axon regrowth, cannot be used due to secondary effects such as weight loss (Winkler et al., Ann Neurol 41, 82-93), uncontrolled cell migration (Williams, Exp Neurol 113, 31-7) and the risk of cancer associated with the abnormal growth of Schwann cells (Eriksdotter Jonhagen et al., Dement Geriatr Cogn Disord 9, 246-57). In spite of intensive research, there is not currently a satisfactory solution for solving the above-mentioned problems, and a new approach is therefore necessary.

New sterol derivatives have already been described, these being compounds which induce neuronal differentiation of pluripotent embryonic tumour cells, survival of motor neurons in culture, and growth and differentiation of adult neuronal progenitors (de Medina et al., 2009, J Med Chem 52, 7765-77) and (2003, Khalifa et al., Biochem Biophys Res Commun 446, 681-6). A person skilled in the art cannot clearly deduce that these compounds will be of benefit for pathologies which, as indicated above, are associated with a neuronal connection problem rather than a problem relating to the number of neurons in the treated zone. Thus, a person skilled in the art will not likely seek to use the sterol derivatives in order to re-establish the connections between the SGNs on the one hand and a signal emitter on the other hand, formed by at least partially functional hair cells or cochlear implant electrodes.

It has now been found, in accordance with the invention, that if these compounds are used on a laboratory animal made deaf by a stress, the transmission of the sound information conveyed in the form of electrical pulse (by the electrodes of a cochlear implant replacing the hair cells) is maintained, the information being transmitted by means of the SGNs towards the brain, moreover without increasing the number of SGNs in said animal.

The present invention consequently relates to a pharmaceutical composition for preventing hearing loss in a subject or for obtaining at least partial therapeutic restoration of the hearing in a treated subject having reduced auditory function prior to treatment, by placing said composition in contact with at least part of the cochlea of the ear having a reduced auditory function, said composition being characterised in that it contains, in a pharmaceutically acceptable vehicle, a significantly active dose of at least one compound of formula (I):

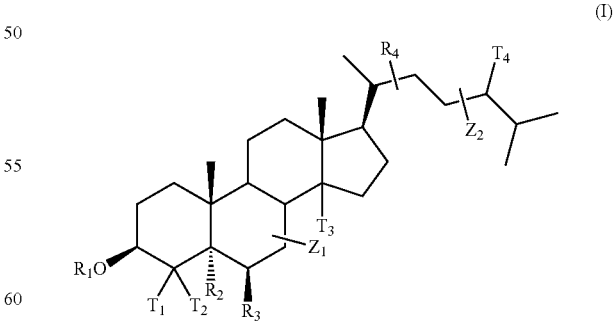

in which formula
$R_1$=H or R—CO, with R=H, $CH_3$ or $C_2H_5$;
$R_2$=H or OH;
$R_3$=—$NR_5R_6$, $R_5$ being H or $(CH_2)_3NH_2$ and $R_6$ being taken from the group formed by —$(CH_2)_4NH_2$;

—$(CH_2)_3NH(CH_2)_4NH_2$;
—$(CH_2)_4NH(CH_2)_3NH_2$;
—$(CH_2)_3NH(CH_2)_4NH(CH_2)_3NH_2$;
—$(CH_2)_3NH_2$, —$(CH_2)_2$-imidazol-4-yl and
—$(CH_2)_2$-indol-3-yl;

$R_4$=H or OH in position 20, 22, 24, 25, 26 or 27, positioned so as to obtain an asymmetric centre of configuration R or S;

$Z_1$ and $Z_2$ are the numbers of double bonds (either 0 or 1) between the atoms C7 and C8 or C22 and C23 respectively;

$T_1$, $T_2$ and $T_3$=H or $CH_3$, independently of each other;

$T_4$=H, $CH_3$, or $C_2H_5$, positioned so as to obtain an asymmetric centre of configuration R or S in position 24 and/or at least one pharmaceutically acceptable salt of at least one compound of formula (I).

Among the compositions defined above, it has been found that the results obtained were particularly interesting for the compounds of the sub-groups in which:

a) the compound(s) of formula (I), contained therein, is (are) defined by $Z_1$=0; $R_1$=H; $R_2$=OH; $R_3$=—$NHR_6$ where $R_6$ is —$(CH_2)_3NH(CH_2)_4NH(CH_2)_3NH_2$ or —$(CH_2)_2$-imidazol-4-yl; $T_1$=$T_2$=$T_3$=H;

b) the compound(s) of formula (I), contained therein, is (are) defined by $Z_1$=0 or 1, $R_1$=H; $R_2$=OH; $R_3$=—$NHR_6$ where $R_6$ is —$(CH_2)_3NH(CH_2)_4NH_2$ or —$(CH_2)_4NH(CH_2)_3NH_2$; $T_1$=$T_2$=$T_3$=H; $R_4$=H or OH in position 22 or 27;

c) the compound of formula (I), contained therein, is defined by $Z_1$=0; $R_1$=acetyl; $R_2$=OH; $R_4$=H; $R_3$=NH—$(CH_2)_2$-imidazol-4-yl and $T_1$=$T_2$=$T_3$=H.

In accordance with a first aspect of the invention, the restoration brought about by the composition according to the invention is an improvement of the efficacy of a cochlear implant previously positioned in the treated subject.

In accordance with a further aspect of the invention, the restoration obtained with the composition according to the invention improves the functionality of the spiral ganglion neurons in the treated subject before at least one therapy intended to stimulate said neurons or the internal and external hair cells has been performed on said subject.

In accordance with a further aspect of the invention, the restoration brought about by the composition according to the invention benefits a subject requiring placement of a cochlear implant due to hearing loss caused by a trauma or a disease, said restoration maintaining the functionality of the spiral ganglion neurons prior to implantation of said cochlear implant.

In accordance with a further aspect of the invention, the composition according to the invention is used to make a subject more able to benefit subsequently from a therapy aimed at restoring all or part of the inner ear, said therapy being selected from the group formed by transplantation of stem cells, regeneration of hair cells by transdifferentiation of supporting cells, by gene transfection, or by gene blocking in any part of the inner ear.

In accordance with a further aspect of the invention, the composition according to the invention is administered orally, intravenously, intratympanically, intracochlearly, on the round or oval window of the cochlea, intracranially or nasally, or on the eardrum.

In accordance with a further aspect of the invention, the composition according to the invention is placed in the inner ear by means of an electrode impregnated with or smeared with said composition, or by means of an electrode having a cannula loaded with said composition or also by means of an electrode made in part of one or more compounds of formula (I).

In accordance with a further aspect of the invention, the restoration obtained by the composition according to the invention benefits a subject for whom the trauma was caused by an ototoxic level of noise, ototoxic agents such as radiation, antibiotics, anti-inflammatories, chemotherapy agents, heavy metals, or the age of the subject.

In accordance with a further aspect of the invention, the composition according to the invention enables a restoration which benefits a subject for whom the hearing loss was caused by a disease taken from the group formed by otitis, Pendred syndrome, Niemann-Pick disease, Smith-Lemli-Opitz syndrome, Stickler syndrome, Alport syndrome, CHARGE syndrome, Jervell and Lange-Nielsen syndrome, Norrie disease, Usher syndrome, Waardenburg syndrome and Perrault syndrome, a neurofibromatosis type 2, or a branchio-oto-renal syndrome.

The present invention also relates to the use of a composition such as that defined above to maintain and/or improve the quality of the connections between the SGNs on the one hand and the hair cells or the electrodes of a cochlear implant on the other hand.

The implementation of the invention is illustrated by three examples, illustrated in a drawing comprising five figures.

FIG. 1 is a diagram relating to the different diseases of the inner ear leading to neurosensory hearing losses which can be remedied by the present invention, and the cell effects relating thereto.

This figure includes three areas: the area on the left shows the synaptic connection S of an HC to an SGN in the case of a subject with no disease of the inner ear. The middle area shows the state of the SGN/HC connections in three cases of dysfunction A, B, C: in dysfunction A the SGN no longer receives information from the synapse S due to a lack of function of the HC (shown in a dotted manner) connected previously to S; in dysfunction B the SGN no longer receives information from the synapse because the latter no longer performs its connection role (left column) and the SGN degenerates (right column); in dysfunction C the SGN no longer has an operational receiving synapse (left column) and the emission originating from the HC therefore cannot supply the SGN, which henceforth degenerates (right column). The area on the right shows the result when products DA or DB are made to act on the elements affected by the dysfunctions A (loss of HC), B (synaptopathy) and C (neuropathies) and the illustrations in the column on the right show the states after treatment and partial recovery of the hearing (the rectangle D indicates electrical stimulation of the SGN).

In the figures, the following abbreviations have been used:
AP: artificial perilymph (Ringer's acetate)
DA: 6β-[2-(1H-imidazol-4-yl)-ethylamino]-cholestane-3β,5β-diol
DB: 6β-[3-(4-aminobutylamino)propylamino]-cholestane-3β,5α-diol
eABR: electrical auditory brainstem response
Neo: neomycin
GDNF: glia cell-line derived neurotrophic factor
SGC: spinal ganglion cell Table 1 summarises the effect of the molecules used in examples 1 to 3 on the density of the SGNs and the electrical auditory brainstem response (eABR).

Hereinafter, the terms "connection" and "synaptic connection" refer to a functional interaction between the spiral ganglion neurons and the hair cells or the electrodes of a cochlear implant enabling an appropriate stimulation of said spiral ganglion neurons.

The term "stress" refers to a cause of loss of functional synaptic connection and/or the loss of the projections of the spiral ganglion neurons.

The studies of examples 1 to 3 were performed on guinea pigs (250-500 g). All the animals were provided with a platinum-iridium electrode inserted into the cochlear in order to mimic a cochlear implant. The experiments were carried out in accordance with the protocol described by Raphael and collaborators (Shinohara et al., 2002, Proc. Nati. Acad. Sci. USA, 99, 1657-60).

EXAMPLE 1: EFFECT OF EARLY TREATMENT WITH A DERIVATIVE OF FORMULA (I) ON THE EXCITABILITY OF THE SPIRAL GANGLION NEURONS (SGNS)

The animals were anaesthetised (10 mg/kg of xylazine and 40 mg/kg of ketamine, administered intramuscularly) and the inner ear was opened postauricularly. A pre-filled cannula containing 24 µl of 10% neomycin sulfate was connected to an osmotic mini-pump (ALZET 2002, DURECT Corp., CA, USA) having a flow rate of 0.5 µl/hour. The cannula penetrated the cochlea in proximity of the round window so as to reach the scala tympani. After 48 hours the cannula was filled either with a solution of 6β-[2-(1H-imidazol-4-yl)-ethylamino]-cholestane-3β,5α-diol (1 µM), or with a solution of 6β-[3-(4-aminobutylamino)propylamino]-cholestane-3β,5α-diol (1 µM), or with GDNF (1 µg/ml), or with artificial perilymph, which served as control. After two weeks, the pump was removed and replaced by a new identical pump, pre-filled in a similar fashion. After another two weeks, the pump was removed and the cannula sealed for two additional weeks. This technique is described in detail on page 1658 of the Shinohara publication identified above.

Figure 1:
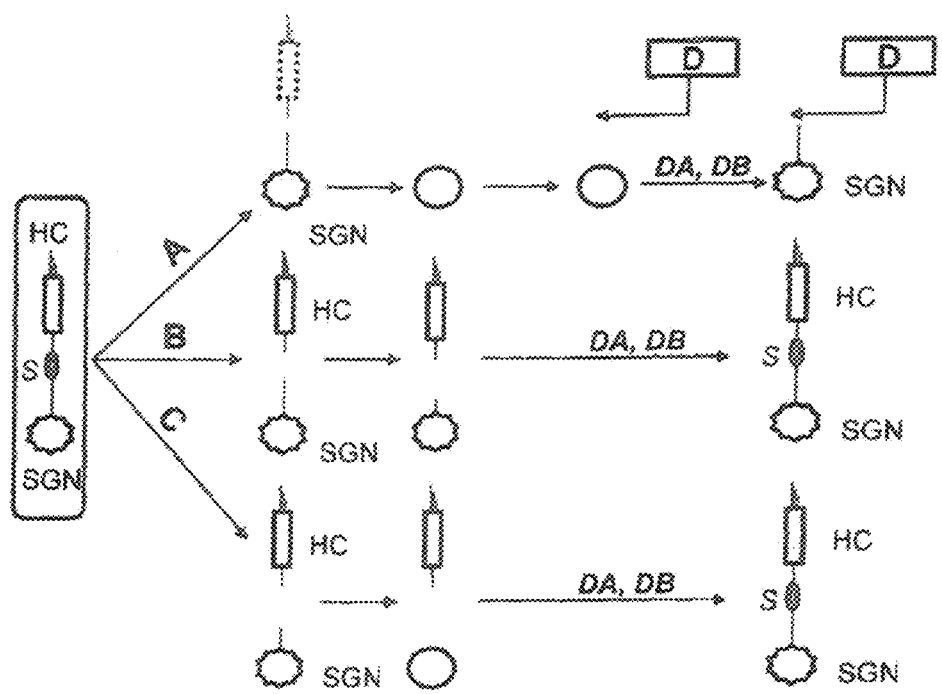
Figure 2:
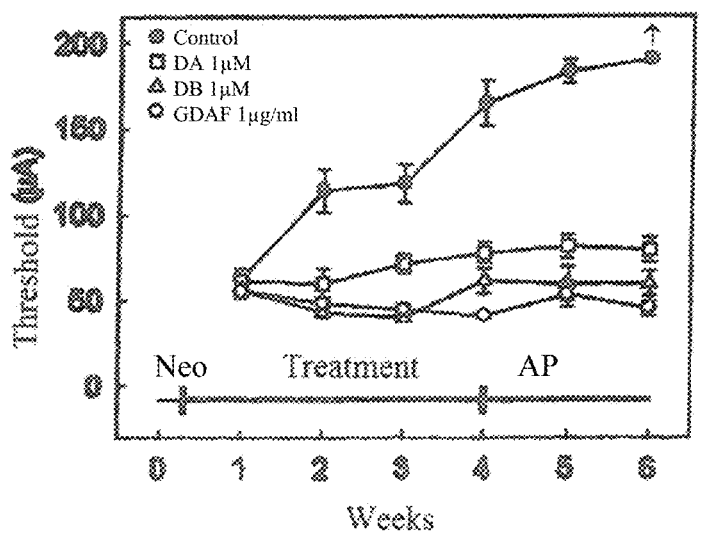
FIG. 2 is a graph showing the curve of progression over time of the electrical auditory brainstem response (eABR) when the treatment with the composition according to the invention starts two days after the start of the induction of the ototoxicity by neomycin.

The measurements of the electrical auditory brainstem response (eABR) thresholds were taken with the aid of an iridium-platinum electrode (Pt—Ir 90%-10%, 250 µm diameter), inserted 1.5 mm into the cochlea scala tympani via the round window at the same time as placement of the pump, a return electrode (Pt—Ir, 125 µm diameter) being placed against the occipital bone, beneath the muscles of the neck. The measurement of the eABR thresholds throughout the experiment did not reveal any significant difference between the groups up to the second week. From then on, there was a significant reduction of the eABR thresholds between the treated groups and the control group (p<0.05 at two weeks and p<0.001 after the fourth week), as shown in FIG. 2. From the sixth week, no eABR could be obtained in the animals in the control group. There was no possible eABR stimulation in the animals placed under the same conditions as defined above, but not treated by the products DA or DB.

EXAMPLE 2: EFFECT OF DELAYED TREATMENT PROVIDED WITH THE DERIVATIVES DA OR DB, USED IN EXAMPLE 1, ON THE EXCITABILITY OF THE SPIRAL GANGLION NEURONS

The procedure used was the same as in example 1, apart from the difference that, following the infusion of neomycin sulfate, the pumps were filled with artificial perilymph for two weeks. At the time of replacement, the pumps were replaced by identical pumps containing either a solution of 6β-[2-(1H-imidazol-4-yl)-ethylamino]-cholestane-3β,5α-diol (1 µM), or a solution of 6β-[3-(4-aminobutylamino)propylamino]-cholestane-3,5α-diol (1 µM), or GDNF (1 µg/ml, or artificial perilymph, which served as control. These pumps were replaced after two weeks by identical pumps, pre-filled with the same solutions for two additional weeks.

Figure 3:
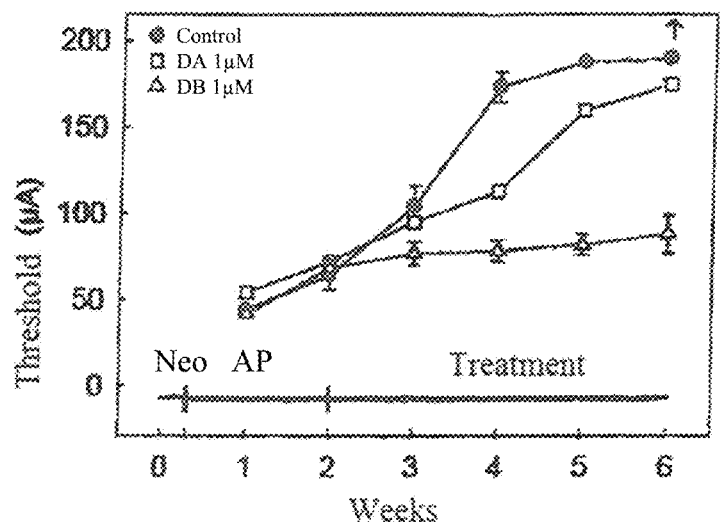
FIG. 3 is a graph showing the curve of progression over time of the electrical auditory brainstem response (eABR) when the treatment with the composition starts sixteen days after the start of the induction of the ototoxicity by neomycin.

The measurements of the electrical auditory brainstem response (eABR) thresholds taken throughout the experiment revealed significant differences between the treated groups and the control group up to the fourth week. From the fifth week, there was no longer a significant difference between the group treated with 6β-[2-(1H-imidazol-4-yl)-ethylamino]-cholestane-3β,5α-diol and the control group, whereas there was a significant difference between the group treated with 6β-[3-(4-aminobutylamino)propylamino]-cholestane-3β,5α-diol and the control group (p<0.01), as shown in FIG. 3. There was no eABR stimulation possible in the animals placed under the same conditions as defined above, but not treated by the products DA or DB.

EXAMPLE 3: QUANTIFICATION OF THE DENSITY OF THE SGNS IN ROSENTHAL'S CANAL

After the final measurement of the eABR threshold, the animals were heavily anaesthetised, intraperitoneally, using sodium pentobarbital (25 mg/kg) and infused intracardially with a saline solution (37° C.), which eliminates blood, then with a cold glutaraldehyde solution (2.5% in a 0.1 M phosphate buffer), which fixes the tissues. The temporal bone was removed, then the bulla was opened to reveal the cochlea. A small window was opened in the apex of the cochlea and the membrane of the round window so as to be able to delicately wash the cochlea with the glutaraldehyde solution. The cochlea was then decalcified in a solution of EDTA (0.1 M in the phosphate buffer) so as to make it possible to make cuts. After decalcification, the cochlea was dehydrated and enclosed in "plastic JB-4" (Polyscience Inc, Warrington, Pa.). The cochlea was sectioned into slices 4 µm thick. Within the modiolus, characterised by a slice in which it is possible to distinguish six sections of Rosenthal's canal, one slice in three was preserved for analysis (which avoids counting the same spiral ganglion neurons a number of times). The slices were placed on slides with "Paragon", coloured with toluidine blue, and prepared for microscopy.

Figure 4:
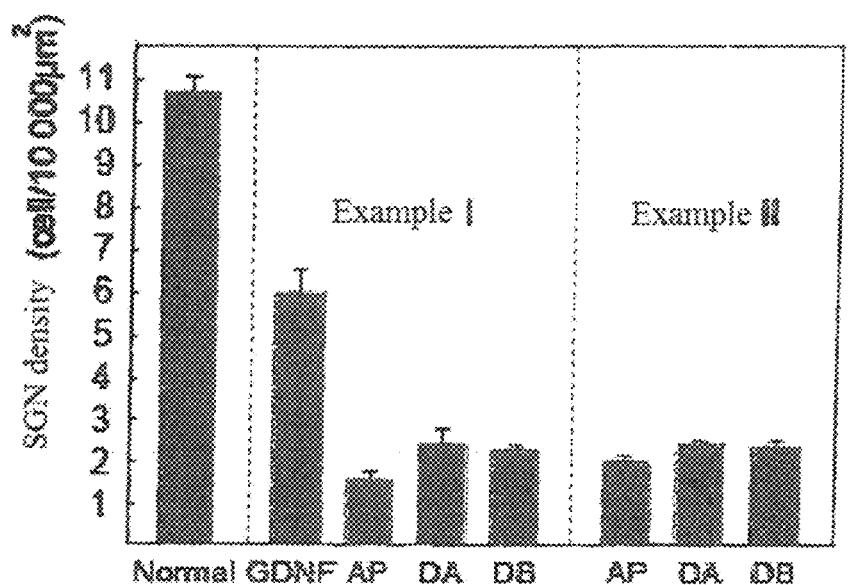
FIG. 4 is a bar chart showing the number of spiral ganglion neurons in the experiments relating to FIGS. 1 and 2 compared to that for an ear not having been exposed to neomycin (first bar on the left in FIG. 4).
Figure 5A:
FIGS. 5A-5C are a series of three photographs of slices of the cochlea taken from the modiolus, illustrating the quantification of the number of spiral ganglion neurons reported in FIG. 4 as well as the axon re-growth brought about by the treatments. For each photograph the nature of the product used for the treatment (AP, DB and GDNF) has been indicated.
Figure 5B:
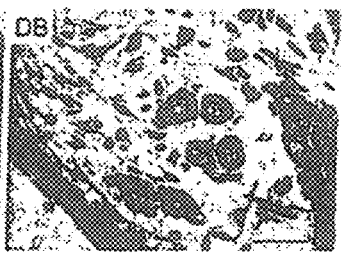
Figure 5C:

The six sections of Rosenthal's channel of six slices were analysed for each group of animals (Sigma Pro Scan) so as to count the spiral ganglion neurons. The criteria selected for an SGN were a cell diameter between 14 and 20 μm with a ring diameter of from 7 to 10 μm. The mean density of SGNs was thus calculated and is shown in FIG. 4; the cuts of Rosenthal's canal are shown in FIG. 5.

For example 1, only the treatment with GDNF led to a significant difference of the number of SGNs compared to the control group treated with the artificial perilymph (P<0.001). For example 2, it can be seen that no delayed treatment leads to a significant difference compared to the control group.

The histological analysis, however, revealed (see FIG. 5), for the animals treated by DB, that the axons of the SGNs appeared thin and long, whereas they were not distinguishable for the animals treated by AP. This explains the efficacy of DB, because the electrical resistance of the neuron decreases as the size of the axon increases (reducing the distance between the transducer of the signal and the neuron).

The invention claimed is:

1. A method for treating hearing in a subject, the method comprising:
placing a composition in contact with at least part of the cochlea of the ear of a subject, said composition being characterised in that it contains, in a pharmaceutically acceptable vehicle, at least one compound of formula (I):

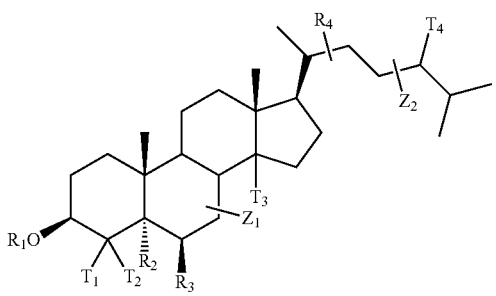

(I)

in which formula $R_1$=H or R—CO, with R=H, $CH_3$ or $C_2H_5$; $R_2$=H or OH; $R_3$=—$NR_5R_6$, $R_5$ being H or —$(CH_2)_3NH_2$ and $R_6$ being taken from the group formed by —$(CH_2)_4NH_2$; —$(CH_2)_3NH(CH_2)_4NH_2$; —$(CH_2)_4NH(CH_2)_3NH_2$; —$(CH_2)_3NH(CH_2)_4NH(CH_2)_3NH_2$; —$(CH_2)_3NH_2$; —$(CH_2)_2$-imidazol-4-yl and —$(CH_2)_2$-indol-3-yl; $R_4$=H or OH in position 20, 22, 24, 25, 26 or 27, positioned so as to obtain an asymmetric centre of configuration R or S; $Z_1$ and $Z_2$ each represent the number of double bonds between the atoms C7 and C8 and C22 and C23 respectively (either 0 or 1); $T_1$, $T_2$ and $T_3$=H or $CH_3$, independently of each other; $T_4$=H, $CH_3$, or $C_2H_5$, positioned so as to obtain an asymmetric centre of configuration R or S in position 24; and/or at least one pharmaceutically acceptable salt of at least one compound of formula (I).

2. The method according to claim 1, characterised in that the compound(s) of formula (I), contained therein, is (are) defined by $Z_1$=O; $R_1$=H;
$R_2$=OH; $R_3$=$NHR_6$ where $R_6$ is —$(CH_2)_3NH(CH_2)_4NH$ $(CH_2)_3NH_2$ or —$(CH_2)_2$-imidazol-4-yl;
$T_1$=$T_2$=$T_3$=H.

3. The method according to claim 1, characterised in that the compound(s) of formula (I), contained therein, is (are) defined by $Z_1$=O or 1, $R_1$=H; $R_2$=OH;
$R_3$=—$NHR_6$ where $R_6$ is —$(CH_2)_3NH(CH_2)_4NH_2$ or —$(CH_2)_4NH(CH_2)_3NH_2$; $T_1$=$T_2$=$T_3$=H; $R_4$=H or OH in position 22 or 27.

4. The method according to claim 1, characterised in that the compound of formula (I) is defined by $Z_1$=O; $R_1$=acetyl; $R_2$=OH; $R_4$=H; $R_3$=NH—$(CH_2)_2$-imidazol-4-yl and $T_1$=$T_2$=$T_3$=H.

5. The method according to claim 1 for improving the transmission of the auditory signal towards the brain from the transducer of the signal (hair cell or electrode).

6. The method according to claim 5 for improving the efficacy of a cochlear implant previously positioned in the subject.

7. The method according to claim 5 for improving the functionality of the spiral ganglion neurons in the subject before at least one therapy intended to stimulate the number and/or the functionality of said neurons or internal and external hair cells has been performed on said subject.

8. The method according to claim 5 for maintaining the functionality of the spiral ganglion neurons prior to implantation of a cochlear implant in the subject, wherein the subject requires the placement of said cochlear implant due to a hearing loss caused by a trauma or a disease.

9. The method according to claim 5 for making the subject more able to benefit subsequently from a therapy aimed at restoring all or part of the inner ear, said therapy being selected from the group formed by transplantation of stem cells, regeneration of hair cells by transdifferentiation of supporting cells, gene transfection, and gene blocking in all or part of the inner ear.

10. The method according to claim 1, characterised in that the subject is a subject for whom a trauma was generated by an ototoxic level of noise, ototoxic agents such as radiation, antibiotics, anti-inflammatories, chemotherapy agents, heavy metals, or the age of the subject.

11. The method according to claim 1, characterised in that the subject is a subject for whom a hearing loss was generated by a disease taken from the group formed by otitis, Pendred syndrome, Niemann-Pick disease, Smith-Lemli-Optiz syndrome, Stickler syndrome, Alport syndrome, CHARGE syndrome, Jervell and Lange-Nielsen syndrome, Norrie disease, Usher syndrome, Waardenburg syndrome and Perrault syndrome, a neurofibromatosis type 2, or a branchio-oto-renal syndrome.

12. The method according to claim 1 for maintaining and/or improving the quality of the connections between the SGNs on the one hand and the hair cells or the cochlear electrodes on the other hand.

13. The method according to claim 1, wherein the subject has reduced auditory function, and the method causes at least partial restoration of the auditory function in the subject.

14. The method according to claim 1, comprising the step of administering the composition orally, intravenously, intratympanically, intracochlearly, on the round or oval window of the cochlea, intracranially or nasally, or on the eardrum.

15. The method according to claim 1, comprising the step of placing the composition in the inner ear using an electrode impregnated with or smeared with said composition, or using an electrode having a cannula loaded with said composition or using an electrode made in part of one or more compounds of formula (I).

* * * * *